(12) United States Patent
Skjæret et al.

(10) Patent No.: US 9,365,482 B2
(45) Date of Patent: Jun. 14, 2016

(54) METHODS OF PREPARING FATTY ACID DERIVATIVES

(71) Applicant: PRONOVA BIOPHARMA NORGE AS, Lysaker (NO)

(72) Inventors: Tore Skjæret, Oslo (NO); Ragnar Hovland, Nesoddtangen (NO)

(73) Assignee: Pronova Biopharma Norge AS, Lysaker (NO)

( * ) Notice: Subject to any disclaimer, the term of this patent is extended or adjusted under 35 U.S.C. 154(b) by 0 days.

(21) Appl. No.: 14/770,870

(22) PCT Filed: Feb. 27, 2014

(86) PCT No.: PCT/IB2014/000954
§ 371 (c)(1),
(2) Date: Aug. 27, 2015

(87) PCT Pub. No.: WO2014/132135
PCT Pub. Date: Sep. 4, 2014

(65) Prior Publication Data
US 2016/0009625 A1    Jan. 14, 2016

Related U.S. Application Data

(60) Provisional application No. 61/770,601, filed on Feb. 28, 2013.

(51) Int. Cl.
*C07C 51/367* (2006.01)
*C07C 29/147* (2006.01)
*C07C 51/47* (2006.01)
*C07C 51/42* (2006.01)

(52) U.S. Cl.
CPC ............. *C07C 51/367* (2013.01); *C07C 29/147* (2013.01); *C07C 51/42* (2013.01); *C07C 51/47* (2013.01)

(58) Field of Classification Search
None
See application file for complete search history.

(56) References Cited

U.S. PATENT DOCUMENTS 8,735,436 B2 * 5/2014 Hovland .............. C07D 263/26
514/376
2013/0345269 A1 * 12/2013 Hovland ................ A61K 31/19
514/376

FOREIGN PATENT DOCUMENTS

WO    WO 2010/128401 A1    11/2010
WO    WO 2012/059818 A1    5/2012

OTHER PUBLICATIONS

Antonucci, Vincent et al., "Toxicological Assessment of 2-Methyltetrahydrofuran and Cyclopentyl Methyl Ether in Support of Their Use in Pharmaceutical Chemical Process Development," Organic Process Research & Development. vol. 15, pp. 939-941 (2011).
International Search Report of International Application No. PCT/IB2014/000954, Sep. 11, 2014.

* cited by examiner

*Primary Examiner* — Yate K Cutliff
(74) *Attorney, Agent, or Firm* — Finnegan, Henderson, Farabow, Garrett & Dunner, LLP

(57) ABSTRACT

Methods for the efficient synthesis of fatty acid derivatives and their intermediates are provided.

20 Claims, No Drawings

METHODS OF PREPARING FATTY ACID DERIVATIVES

This application is a national stage filing under 35U.S.C. §371of International Application No PCT/IB2014/000954filed on Feb. 27, 2014, which claims priority to U.S. Provisional Application No. 61/770,601 filed on Feb. 28, 2013, all of which are herein by reference in their entireties.

TECHNICAL FIELD

The present disclosure relates to a method of preparing fatty acid derivatives. Particularly, the present disclosure relates to a method of preparing 2-((5Z,8Z,11Z,14Z,17Z)-icosa-5,8,11,14,17-pentaenyloxy)butanoic acid (3)

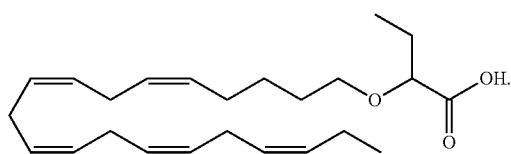

(3)

BACKGROUND

Polyunsaturated fatty acids (PUFAs), such as EPA and DHA, have effects on diverse physiological processes impacting normal health and chronic diseases, such as the regulation of plasma lipid levels, cardiovascular and immune functions, insulin action, neuronal development, and visual function. Some derivatives of polyunsaturated fatty acids have also been shown to have beneficial biological profiles.

The present disclosure provides new methods for preparing 2-((5Z,8Z,11Z,14Z,17Z)-icosa-5,8,11,14,17-pentaenyloxy)butanoic acid (3). This compound and other similar compounds as well as their syntheses are disclosed in WO 2010/128401 describing, in general, that fatty alcohols may be prepared directly from carboxylic esters of naturally occurring fatty acids, such as eicosapentaenoic acid (EPA) by reduction with a reducing agent like lithium aluminum hydride (LAH) or diisobutyl aluminum hydride (DIBAL-H). According to WO 2010/128401 the acid (3) is prepared by a synthesis wherein the fatty alcohol (5Z,8Z,11Z,14Z,17Z)-icosa-5,8,11,14,17-pentaen-1-ol (2) is substituted with t-butyl 2-bromobutyrate, and in a following step the t-butyl group is removed to obtain the desired 2-((5Z,8Z,11Z,14Z,17Z)-icosa-5,8,11,14,17-pentaenyloxy)butanoic acid (3).

The method described above has several disadvantages. It requires high amounts of reagents, both solvents and starting materials. And the staring fatty acid esters prepared from, for example, fish oil, and especially highly purified EPA esters, are rather expensive. Even when optimized, the above described synthesis of 2-((5Z,8Z,11Z,14Z,17Z)-icosa-5,8,11,14,17-pentaenyloxy)butanoic acid (3) from EPA ethyl ester (1) provides less than 25% in overall yield starting from about 5 kg EPA ethyl ester (purity ≥97%). Thus, from a commercial point of view it would clearly be highly advantageous to increase the overall yield and decrease the amount waste generated. Another important factor is achieving a desirable purity profile of the final product when the synthesis is scaled up. Because most organic reactions generate side-products, it is desirable to obtain a product that can easily be purified.

The method provided herein reduces the amounts of reagents and solvents and generates less waste compared to the process disclosed in WO 2010/128401. In addition, the present method produces 2-((5Z,8Z,11Z,14Z,17Z)-icosa-5,8,11,14,17-pentaenyloxy)butanoic acid (3) in a higher overall yield and with an improved purity profile.

It is to be understood that both the foregoing general description and the following detailed description are exemplary and explanatory only and are not restrictive of the present disclosure, as claimed.

DETAILED DESCRIPTION

Particular aspects of the disclosure are described in greater detail below. The terms and definitions as used in the present application and as clarified herein are intended to represent the meaning within the present disclosure.

The singular forms "a," "an," and "the" include plural reference unless the context dictates otherwise.

The terms "approximately" and "about" mean to be nearly the same as a referenced number or value. As used herein, the terms "approximately" and "about" should be generally understood to encompass ±10% of a specified amount, frequency or value.

The present disclosure relates to a process for preparing 2-((5Z,8Z,11Z,14Z,17Z)-icosa-5,8,11,14,17-pentaenyloxy)butanoic acid (3) from an EPA derivative of formula (I) comprising the steps of a) reducing the EPA derivative of formula (I):

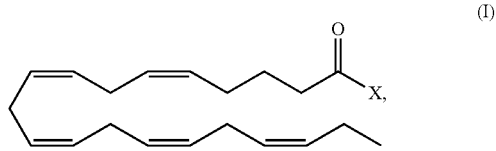

(I)

wherein —C(=O)X represents a carboxylic acid or a carboxylic ester, to its corresponding alcohol (5Z,8Z,11Z,14Z,17Z)-icosa-5,8,11,14,17-pentaen-1-ol (2) by reduction with a reducing agent

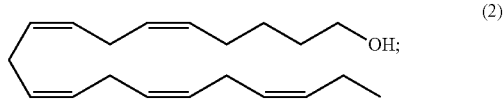 [SMILES: CC/C=C\C/C=C\C/C=C\C/C=C\C/C=C\CCCCO]

(2)

b) isolating the alcohol (2) from step a);
c) reacting the isolated alcohol (2) from step b) with 2-bromobutyric acid to form 2-((5Z,8Z,11Z,14Z,17Z)-icosa-5,8,11,14,17-pentaenyloxy)butanoic acid (3)

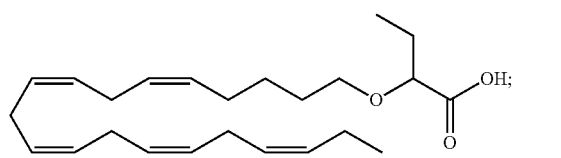

(3)

d) isolating 2-((5Z,8Z,11Z,14Z,17Z)-icosa-5,8,11,14,17-pentaenyloxy)butanoic acid (3) from step c); and e) optionally purifying 2-((5Z,8Z8Z,11Z,14Z,17Z)-icosa-5,8,11,14,17-pentaenyloxy)butanoic acid (3).

As mentioned above the group —C(=O)X of the EPA derivative of formula (I) represents a carboxylic acid or a carboxylic ester. In one embodiment —C(=O)X is a carboxylic acid, that is the compound of formula (I) is eicosapentaenoic acid (EPA). In another embodiment —C(=O)X represents a carboxylic ester. In one embodiment the carboxylic ester is chosen from a methyl ester, ethyl ester, and propyl ester, that is the EPA derivative of formula (I) may be an EPA methyl ester, EPA ethyl ester, or EPA propyl ester. In one embodiment —C(=O)X represents a $C_1$-$C_3$ carboxylic ester. In a at least one embodiment, the EPA derivative of formula (I) is EPA ethyl ester (1)

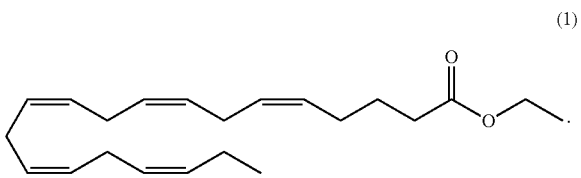 [SMILES: CC/C=C\C/C=C\C/C=C\C/C=C\C/C=C\CCCC(=O)OCC]

(1)

The EPA derivative of formula (I) used may be less than 99% pure, for example, its purity may be less than 98%, less than 95%, less than 90%, less than 85%, less than 80%, less than 75%, less than 70%, less than 65%, less than 60%, less than 55%, less than 50%, less than 45%, or less than 40% pure. In at least one embodiment, the EPA derivative of formula (I) is about 98% pure (by GC). In at least one embodiment the EPA derivative of formula (I) is commercially available.

The EPA ethyl ester (1) used may be less than 99% pure, for example, its purity may be less than 98%, less than 95%, less than 90%, less than 85%, less than 80%, less than 75%, less than 70%, less than 65%, less than 60%, less than 55%, less than 50%, less than 45%, or less than 40% pure. In at least one embodiment, the EPA ethyl ester is about 98% pure. In at least one embodiment, the EPA ethyl ester is about 97% pure. In at least one embodiment the EPA ethyl ester used is commercially available.

It is foreseen that the EPA derivative of formula (I), such as EPA ethyl ester (1), of a lower purity than 60% may be used and possibly present a cost-effective and efficient alternative to the use of high-purity EPA derivatives, particularly on a large scale, provided that an efficient and competitive purification method is available.

The EPA derivative of formula (I) may be derived from a vegetable, microbial, and/or animal source. In at least one embodiment the EPA derivative is EPA and may be derived from a vegetable, microbial, and/or animal source. In at least one embodiment the EPA derivative is EPA methyl ester and may be derived from a vegetable, microbial, and/or animal source. In at least one embodiment the EPA derivative is EPA ethyl ester (1) and may be derived from a vegetable, microbial, and/or animal source. In at least one embodiment the EPA derivative is EPA propyl ester and may be derived from a vegetable, microbial, and/or animal source. In at least one embodiment, the animal source is a marine oil.

In at least one embodiment, the marine oil is a fish oil.

Suitable reducing agents for reduction of the EPA derivative of formula (I) include, but are not limited to, lithium aluminum hydride (LAH), DTBAL-H (iBu$_2$AlH), and diborane (B$_2$H$_6$). In one embodiment, the EPA derivative of formula (I) is reduced using lithium aluminum hydride (LAH). In at least one embodiment, EPA ethyl ester (1) is reduced using lithium aluminum hydride (LAH). In another embodiment, EPA methyl ester is reduced using lithium aluminum hydride (LAH). In another embodiment, EPA propyl ester is reduced using lithium aluminum hydride (LAH). In still another embodiment, EPA is reduced using lithium aluminum hydride (LAH).

Suitable solvents for the reduction of the EPA derivative of formula (I) such as EPA ethyl ester include tetrahydrofuran (THF), diethyl ether, methyl tert-butylether (MTBE), toluene, 1,4-dioxane, 2-methyl tetrahydrofuran (MeTHF), or a mixture thereof. In at least one embodiment suitable solvents for the reduction of the EPA derivative of formula (I) include THF, MTBE, toluene, or a mixture thereof. In one embodiment the EPA derivative is reduced in the presence of THF. In at least one embodiment, EPA ethyl ester (1) is reduced in the presence of THF. In a further embodiment EPA ethyl ester (1) is reduced using LAH in the presence of THF. In one embodiment a co-solvent such as toluene may be present. In at least one embodiment LAH may be provided as a 15% solution of LAH in a THF:toluene (2.4:1) mixture.

The reduction of the EPA derivative of formula (I) such as EPA ethyl ester (1) to (5Z,8Z,11Z,14Z,17Z)-icosa-5,8,11,14,17-pentaen-1-ol (2) according to step a) may be carried out under various temperature conditions. For example, in at least one embodiment, EPA ethyl ester (1) is reduced at ambient temperature of about 23° C. In another embodiment, EPA ethyl ester (1) is reduced at a temperature below 23° C. In at least one embodiment the reduction of the EPA derivative of formula (I), such as EPA ethyl ester (1), is carried out at a temperature ranging from 0° C. to 15° C.

The alcohol (2) formed in step a) is isolated in step b) by any suitable method. In at least one embodiment step b) comprises extractive work-up after quenching of the reaction. Useful reagents for quenching the reaction include, for example, various hydride acceptors (oxidizing agents) such as acids (proton donors), esters, aldehydes, and ketones. In at least one embodiment the reaction is quenched by adding ethyl acetate (EtOAc) and ammonium chloride. In one embodiment the ammonium chloride is added as a saturated aqueous solution of ammonium chloride. The pH of the aqueous phase is then adjusted to about 2 by addition of an acidic solution. Suitable acidic solutions may for example comprise aqueous solutions of HCl or $H_2SO_4$. In one embodiment the acid solution is a 6M aqueous solution of HCl. Then the organic phase is washed with brine and evaporated. Finally, the toluene content of the work-up mixture is adjusted to between 0-30 w/w %, such as 20-30 w/w %.

(5Z,8Z,11Z,14Z,17Z)-Icosa-5,8,11,14,17-pentaen-1-ol (2) made by this method may be obtained in greater than 85% purity, such as greater than 90%, or greater than 95% purity after step b). The starting material may be completely transformed into the alcohol (2), and the yield is at least 90%, such as at least 95%.

(5Z,8Z,11Z,14Z,17Z)-Icosa-5,8,11,14,17-pentaen-1-ol (2) made by the method of the present disclosure is a useful intermediate for the preparation of fatty acid derivatives, including 2-((5Z,8Z,11Z,14Z,17Z)-icosa-5,8,11,14,17-pentaenyloxy)butanoic acid (3).

The use of (5Z,8Z,11Z,14Z,17Z)-icosa-5,8,11,14,17-pentaen-1-ol (2) prepared from the EPA derivative of formula (I) such as EPA ethyl ester (1) using the method disclosed herein provides a cost-effective and efficient synthesis of 2-((5Z,8Z,11Z,14Z,17Z)-icosa-5,8,11,14,17-pentaenyloxy)butanoic acid (3). In addition, direct alkylation of (5Z,8Z,11Z,14Z,17Z)-icosa-5,8,11,14,17-pentaen-1-ol (2) with 2-bromobutyric acid is advantageous over other reported methods. Such advantages include improved control of the alkylation process, higher yields, less chemical steps, less waste, lower cost, and an overall more efficient process. These advantages are especially useful for performing large scale synthesis of compound (3). Furthermore, the method of the present disclosure does not use chlorinated solvents, which is beneficial for the environment. (V. Antonucci et al. *Org. Process Res. Dev.* (2011) 15: 939-941.)

The direct alkylation reaction according to the present disclosure may be conducted in the presence of a base. In at least one embodiment, the direct alkylation reaction of step c) is carried out in the presence of a base. Suitable bases include, but are not limited to, NaOtBu, NaOH, NaOEt, or NaH. In at least one embodiment, the base includes NaOtBu or NaOH. In at least one embodiment the base is NaOtBu. In at least one embodiment the base is a solution of NaOtBu in MTBE. In at least one embodiment the base is a solution of 5-30% of NaOtBu in MTBE, such as 10-20% of NaOtBu in MTBE. e.g. 17% of NaOtBu in MTBE.

The direct alkylation reaction may be conducted in the presence of solvent. In at least one embodiment, the reaction of step c) is carried out in the presence of a solvent or mixture of solvents. Suitable solvents include dimethylformamide (DMF), N-methyl-2-pyrrolidone (NMP), THF, toluene, xylene, methyl tert-butyl ether (MTBE), 2-methyltetrahydrofuran (2-MeTHF), diethyl ether, dimethyl sulfoxide (DMSO), tert-butanol (t-BuOH), or mixtures thereof.

In at least one embodiment, the solvent used in step c) is tetrahydrofuran (THF), methyl tert-butyl ether (MTBE), toluene, or mixtures thereof. In at least one embodiment step c) is carried out in a mixture of THF and MTBE. In at least one embodiment the solvent used in step c) is THF. Alternatively, the solvent is MTBE.

The direct alkylation reaction of step c) may be carried out in several ways. In at least one embodiment the solvent such as THF, the alcohol (2) and 2-bromobutyric acid are charged simultaneously into the reaction vessel. In another embodiment (5Z,8Z,11Z,14Z,17Z)-icosa-5,8,11,14,17-pentaen-1-ol (2) may, for example, be present in a solution of a solvent or solvents. The base may be added directly to that solution. Alternatively, the base may be added to the solution of (2) as a solution in the same or a different solvent. Likewise, the 2-bromobutyric acid may be added neat, that is without solvent, or alternatively may be added to the reaction vessel in a solution of a solvent or mixture of solvents. In at least one embodiment, the base is added to a solvent or solvent mixture and added to the reaction of step c) as a solution or suspension.

The 2-bromobutyric acid may be added to the reaction in step c) in one or more portions. For example, 2-bromobutyric acid may be added to the reaction in one, two, three, four, five or more portions. In at least one embodiment, the 2-bromobutyric acid is added in two or more portions. In at least one embodiment 2-bromobutyric acid may be added continuously to the reaction mixture. In at least one embodiment 2-bromobutyric acid may be added in a combination of batch wise and continuous addition to the reaction mixture.

The base may likewise be added in one or more portions to the reaction in step c). For example, a solution of NaOtBu in MTBE may be added to the reaction in one, two, three, four, five, six, seven or more portions. In at least one embodiment, a solution of NaOtBu in MTBE may be added to the reaction in step c) in three or more portions. In at least one embodiment, a solution of NaOtBu in MTBE may be added continuously to the reaction in step c). In at least one embodiment a solution of NaOtBu in MTBE may be added in a combination of batch wise and continuous addition to the reaction in step c). In another embodiment, NaOtBu may be added to the reaction in step c) in solid form.

In at least one embodiment, the portions are added over a time period of about 30 to 60 minutes. In one embodiment the portions are added over a time period of about 30 minutes. In one embodiment the portions are added over a time period of about 60 minutes. In at least one embodiment the portions are added with about 30 minutes between additions. In at least one embodiment, the portions are added with at least 30 minutes, such as 60 minutes, between additions. Gradual addition of the portions allows for improved control of the alkylation process and results in lower amounts of impurities.

The direct alkylation reaction of step c) may be carried out under various temperature conditions. For example, in at least one embodiment, the direct alkylation reaction of step c) is carried out at ambient temperature of about 23° C. In another embodiment, the direct alkylation reaction of step c) is carried out at a temperature below 23° C. In at least one embodiment the direct alkylation reaction of step c) is carried out at a temperature ranging from 5° C. to 15° C., such as 5° C. to 10° C.

The isolation in step d) may be carried out by various methods. In at least one embodiment, step d) comprises aqueous extraction, either batchwise or in a continuous fashion (i.e., countercurrent extraction (CCE) or countercurrent chromatography (CCC) (including HPCCC and HSCCC)). In at least one embodiment, the reaction is being quenched by the addition of an acid having a low content of water to the reaction mixture of step c) to avoid conjugation, cis/trans isomerization, or both, of the product. In one embodiment the acid is formic acid. In one embodiment the temperature during acid addition is about 5° C. to 10° C. Then, water is added to the reaction mixture of step c). In one embodiment the temperature during water addition is about 5° to 10° C. The pH is then adjusted to a pH below 2.5. In one embodiment the pH is adjusted to about 2-2.5. In one embodiment the pH is adjusted by a 1:1 mixture of concentrated HCl and water. The phases are separated and the aqueous phase is extracted with a suitable organic solvent one or more times. Appropriate solvents may be MTBE, toluene, heptane, pentane, 2-methyltetrahydrofuran, methyl cyclohexane, or mixtures thereof. In one embodiment the solvent is MTBE. In at least one embodiment the combined organic phase is washed with water one or more times. In at least one embodiment the combined organic phase is washed with water at least one time, preferably three times. The organic phase may then be dried over sodium sulfate and filtered through diatomaceous earth, such as celite, and then the solvent is evaporated to obtain crude 2-((5Z,8Z,11Z,14Z,17Z)-icosa-5,8,11,14,17-pentaenyloxy)butanoic acid (3)

According to one embodiment (step d1), the crude 2-((5Z,8Z,11Z,14Z,17Z)-icosa-5,8,11,14,17-pentaenyloxy)butanoic acid (3) may further be dissolved in a suitable organic solvent such as 2-methyltetrahydrofuran, MTBE, toluene, heptane, pentane, methyl cyclohexane, or mixtures thereof. In one embodiment the residue is dissolved in 2-methyltetrahydrofuran. The dissolved residue is washed sequentially with saturated solutions of NaHCO$_3$(aq) and NaCl(aq) one or more times. Water and 2-methyltetrahydrofuran are added to the organic phase and the pH is adjust to above 8, such as pH 12-13, to transfer the product to the aqueous phase before separating the phases. In one embodiment the pH is adjusted by adding a 50% aqueous solution of NaOH. The aqueous phase is washed with a suitable organic solvent such as 2-methyl tetrahydrofuran, MTBE, toluene, heptane, pentane, methyl cyclohexane, or mixtures thereof. In one embodiment the aqueous phase is washed with 2-methyl tetrahydrofuran.

The aqueous phase is clarified by use for instance charcoal and Celite, and the pH is adjusted to about 2-2.5 with an acid, e.g., HCl(aq). In one embodiment the pH is adjusted by concentrated HCl. The product is extracted into an organic solvent and washed with water. In one embodiment the organic solvent is methyl tert-butyl ether (MTBE). The solvents are evaporated. The residue might further be dissolved in an organic solvent. In one embodiment the solvent is pentane. The dissolved product may further be clarified with silica. A stabilizer (e.g., butylated hydroxyanisole (BHA) or 3,5-di-tert-butyl-4-hydroxytoluene (BHT)) may be added to the product before evaporation in vacuum. In one embodiment the stabilizer is BHA. The final product should be kept under inert atmosphere, protected from light and moisture.

Alternatively, according to one embodiment (step d2), crude 2-((5Z,8Z,11Z,14Z,17Z)-icosa-5,8,11,14,17-pentaenyloxy)butanoic acid (3) is being purified by CCE. The organic phase is a solvent or a solvent mixture suitable for CCE (e.g., MTBE, toluene, pentane, hexane, heptane, ethyl acetate, methyl cyclohexane, 2-methyltetrahydrofuran or toluene, or a mixture thereof). The organic phase may contain an acid (e.g., formic acid, acetic acid or trifluoroacetic acid (TFA)) or a base (e.g. triethylamine). In one embodiment the residue is dissolved in pentane, e.g., to give a 5-50 w/w % solution in pentane, such as a 10 w/w % solution in pentane. The aqueous phase is water or an aqueous solution of e.g., an alcohol (e.g., methanol, ethanol, propanol, butanol), acetonitrile or acetone. The aqueous phase may contain an acid (e.g., formic acid, acetic acid or TFA) or a base (e.g. triethylamine). In one embodiment the aqueous solution is of methanol, such as a solution of 67% aqueous methanol. The phases are applied to the CCE equipment at appropriate flow rates. The CCE is continued/repeated until the level of impurities, such as 2-bromo butyric acid and crotonic acid comply with ICH guidelines (ICH Topic Q 3 B (R2) Impurities in New Drug Products). If applicable, the appropriate fractions are pooled and then concentrated in vacuo. The residue may further be dissolved in a suitable organic solvent (e.g., 2-methyltetrahydrofuran, MTBE, toluene, heptane, pentane, or methyl cyclohexane). In one embodiment the residue is dissolved in 2-methyltetrahydrofuran. Water or an aqueous solution of e.g., an alcohol (e.g., methanol, ethanol, propanol, butanol), acetonitrile or acetone is added to the organic phase. In one embodiment the solution is water and the pH Is adjusted to above 8, such as pH 12-13, to transfer the product to the aqueous phase before separating the phases. In one embodiment the pH is adjusted by adding a 50% aqueous solution of NaOH. The aqueous phase is washed with a suitable organic solvent (e.g., 2-methyl tetrahydrofuran, MTBE, toluene, heptane, pentane, methyl cyclohexane, or mixtures thereof). In one embodiment the aqueous phase is washed with 2-methyl tetrahydrofuran. The aqueous phase may be clarified by use of charcoal and Celite, and the pH is adjust to below 2.5, such as 2-2.5, with an acid. e.g., HCl(aq). In one embodiment the pH is adjusted by concentrated HCl. The product is extracted into a suitable organic solvent (e.g., 2-methyltetrahydrofuran, MTBE, toluene, heptane, pentane, methyl cyclohexane, or mixtures thereof) and washed with water. In one embodiment the organic solvent is MTBE. The solvents are evaporated in vacuo. The residue might be dissolved in a suitable organic solvent (e.g., 2-methyltetrahydrofuran, MTBE, toluene, heptane, pentane, methyl cyclohexane, or mixtures thereof). In one embodiment the solvent is pentane. The dissolved product may further be clarified with silica. A stabilizer (e.g., BHA or BHT) may be added to the product before evaporation in vacuo. In one embodiment the stabilizer is BHA. The final product should be kept under inert atmosphere, protected from light and moisture.

Alternatively, according to one embodiment (step d3), crude 2-((5Z,8,11Z,14Z,17Z)-icosa-5,8,11,14,17-pentaenyloxy)butanoic acid (3) is being purified by CCE. The organic phase is a solvent or a solvent mixture suitable for CCE (e.g., MTBE, toluene, pentane, hexane, heptane, ethyl acetate, methyl cyclohexane, 2-methyltetrahydrofuran or toluene, or a mixture thereof). The organic phase may contain an acid (e.g., formic acid, acetic acid or trifluoroacetic acid (TFA)) or a base (e.g. triethylamine). In one embodiment the residue is dissolved in pentane, e.g., to give a 5-50 w/w % solution in pentane, such as a 10 w/w % solution in pentane. The aqueous phase is water or an aqueous solution of e.g., an alcohol (e.g., methanol, ethanol, propanol, butanol), acetonitrile or acetone. The aqueous phase may contain an acid (e.g., formic acid, acetic acid or TFA) or a base (e.g. triethylamine). In one embodiment the aqueous solution is of methanol, such as a solution of 67% aqueous methanol. The phases are applied to the CCE equipment at appropriate flow rates. The CCE is continued/repeated until the level of impurities, such as 2-bromo butyric acid and crotonic acid comply with ICH guidelines (ICH Topic Q 3 B (R2) Impurities in New Drug Products). If applicable, the appropriate fractions are pooled and then concentrated in vacuo. The residue may further be dissolved in a suitable organic solvent (e.g., 2-methyltetrahydrofuran, MTBE, toluene, heptane, pentane, methyl cyclohexane, or mixtures thereof). In one embodiment the residue is dissolved in pentane. (If the solvent/eluent used to carry 2-((5Z,8Z,11Z,14Z,17Z)-icosa-5,8,11,14,17-pentaenyloxy) butanoic acid (3) through the CCE is pentane, its volume may only be adjusted, either by concentration or by addition of pentane, to an appropriate level). To the pentane solution is added a suitable co-solvent (e.g., 2-methyltetrahydrofuran, MTBE, toluene, heptane or methyl cyclohexane). In one embodiment the solvent is MTBE. To this solution is then added water or an aqueous solution of e.g., an alcohol (e.g., methanol, ethanol, propenol, butanol), acetonitrile or acetone. In one embodiment the solution is added methanol and water, and the pH is adjust to above 8, such as pH 12-13, to transfer the product to the aqueous phase before separating the phases. In one embodiment the pH is adjusted by a base, e.g., NaOH. In one embodiment a 40% aqueous solution of NaOH is added. The aqueous phase is washed with a suitable organic solvent (e.g., 2-methyl tetrahydrofuran, MTBE, toluene, heptane, pentane, methyl cyclohexane, or mixtures thereof). In one embodiment the aqueous phase is washed with MTBE. The aqueous phase may be clarified by use of charcoal and Celite. The aqueous phase is then added a suitable organic solvent (e.g., MTBE, toluene, heptane, pentane, 2-methyltetrahydrofuran, or methyl cyclohexane). In one embodiment the solvent is pentane. The pH is adjusted to a pH below 2.5. In one embodiment the pH is adjusted to about 2-2.5 with HCl(aq). In one embodiment the pH is adjusted by a 1:1 mixture of concentrated HCl and water. The phases are agitated and separated. The aqueous phase may be extracted with the organic solvent mentioned above one or more times. The pooled organic solvents may be washed with water and/or brine. The solvents are evaporated. The residue might further be dissolved in an appropriate organic solvent. In one embodiment the solvent is pentane. The dissolved product may further be clarified with silica. A stabilizer (e.g., BHA or BHT) may be added to the product before evaporation in vacuo. In one embodiment the stabilizer is BHA. The final product should be kept under inert atmosphere, protected from light and moisture.

Alternatively, according to one embodiment (step d4), crude 2-(5Z,8Z,11Z,14Z,17Z)-icosa-5,8,11,14,17-pentaenyloxy)butanoic acid (3) is purified by CCC. The organic phase is a solvent or a solvent mixture suitable for CCC (e.g., MTBE, toluene, pentane, hexane, heptane, ethyl acetate, methyl cyclohexane, 2-methyltetrahydrofuran or toluene, or a mixture thereof). The organic phase may contain an acid (e.g., formic acid, acetic acid or TFA) or a base (e.g. triethylamine). In one embodiment the organic solvent is hexane containing 0.1% acetic acid. The aqueous phase is water or an aqueous solution of e.g., an alcohol (e.g., methanol, ethanol, propanol, butanol), acetonitrile or acetone. The aqueous phase may contain an acid (e.g., formic acid, acetic acid or TFA) or a base (e.g. triethylamine). In one embodiment the aqueous solvent is an aqueous solution of methanol containing 0.1% acetic acid, such as a solution of 15% water in methanol, containing 0.1% acetic acid. The CCC may be run either at reverse phase mode, normal phase mode or at dual-mode, at an appropriate flow rate. The purification is continued/repeated until desired purity of 2-((5Z,8Z,11Z,14Z,17Z)-icosa-5,8,11,14,17-pentaenyloxy)butanoic acid (3) is obtained, i.e. until an appropriate level of impurities is reached. The dissolved product may be clarified with charcoal and/or silica during the process. A stabilizer (e.g., BHT or BHA) may be added to the product before evaporation in vacuo. In one embodiment the stabilizer is BHA. The final product should be kept under inert atmosphere, protected from light and moisture.

Alternatively, according to one embodiment (step d5), crude 2-((5Z,8Z,11Z,14Z,17Z)-icosa-5,8,11,14,17-pentaenyloxy)butanoic acid (3) is purified by combining CCE and CCC as described above. The purification is continued until the level of impurities comply with the drug substance specification for 2-((5Z,8Z,11Z,14Z,17Z)-icosa-5,8,11,14,17-pentaenyloxy)butanoic acid (3). The dissolved product may be clarified with charcoal and/or silica during the process. A stabilizer (e.g., BHT or BHA) may be added to the product before evaporation in vacuo. In one embodiment the stabilizer is BHA. The final product should be kept under inert atmosphere, protected from light and moisture.

Alternatively, according to one embodiment (step d6), crude 2-((5Z,8Z,11Z,14Z,17Z)-icosa-5,8,11,14,17-pentaenyloxy)butanoic acid (3) is purified by combining batchwise extractions and CCC as described above. The purification is continued until the level of impurities comply with the drug substance specification for 2-((5Z,8Z,11Z,14Z,17Z)-icosa-5,8,11,14,17-pentaenyloxy)butanoic acid (3). The dissolved product may be clarified with charcoal and/or silica during the process. A stabilizer (e.g., BHT or BHA) may be added to the product before evaporation in vacuo. In one embodiment the stabilizer is BHA. The final product should be kept under inert atmosphere, protected from light and moisture.

Suitable techniques for further purification of 2-((5Z,8Z,11Z,14Z,17Z)-icosa-5,8,11,14,17-pentaenyloxy)butanoic acid (3) of step e) comprise chromatography (e.g., by use of flash chromatography, HPLC, supercritical fluid, simulated moving bed (SMB), Multicolumn Countercurrent Solvent Gradient Purification (MCSGP), and High Performance Counter Current Chromatography (HPCCC)) or distillation, through methods known to the person skilled in the art.

Suitable techniques for the chiral resolution of 2-((5Z,8Z,11Z,14Z,17Z)-icosa-5,8,11,14,17-pentaenyloxy)butanoic acid (3) of step e) comprise separation by means of chiral resolving agents and by column chromatography (e.g., by use of flash chromatography, HPLC, supercritical fluid, simulated moving bed (SMB), Multicolumn Countercurrent Solvent Gradient Purification (MCSGP), and High Performance Counter Current Chromatography (HPCCC)) or distillation, or by chiral column chromatography, through methods known to the person skilled in the art. One example of chiral resolution of 2-((5Z,8Z,11Z,14Z,17Z)-icosa-5,8,11,14,17-pentaenyloxy)butanoic acid (3) using a chiral resolving agent is described in examples 3-5 of WO 2012/059818.

Because PUFAs are highly unsaturated, exposure of them to oxygen should be controlled. Thus, in at least one embodiment, steps a)-e) of the present disclosure are conducted to minimize exposure to oxygen. In at least one embodiment, steps a)-e) are conducted in an inert atmosphere, such as nitrogen or argon gas.

In at least one embodiment, 2-((5Z,8Z,11Z,14Z,17Z)-icosa-5,8,11,14,17-pentaenyloxy)butanoic acid (3) is obtained in an overall yield of at least 50% starting from EPA ethyl ester (1), such as at least 55%, at least 60%, at least 65%, at least 70%, at least 75% or at least 80%.

In at least one embodiment, 2-((5Z,8Z,11Z,14Z,17Z)-icosa-5,8,11,14,17-pentaenyloxy)butanoic acid (3) is obtained in at least 90% purity, such as at least 95% purity, such as at least 97% purity, or at least 99% purity.

The reaction steps may be carried out on a large scale. In at least one embodiment, "large scale" refers to the use of at least 1 kg of a starting material, intermediate, or reagent, such as the use of at least 5 kg, at least 8 kg, at least 10 kg, at least 25 kg, at least 50 kg, at least 100 kg, at least 250 kg, or at least 500 kg.

EXAMPLES

Abbreviations used herein denote the following compounds, reagents and substituents: sodium tert-butoxide (NaOtBu or tBuONa); sodium hydroxide (NaOH); tetrahydrofuran (THF); methyl tert-butyl ether (MTBE); deionized water (DI water); butylated hydroxyanisole (BHA); lithium aluminum hydride (LAH). Other abbreviations used herein are: aqueous (aq.), equivalents (eq.). If an abbreviation is not defined, it has its generally accepted meaning.

The disclosure will now be further described by the following non-limiting examples, in which standard techniques known to the skilled chemist and techniques analogous to those described in these examples may be used where appropriate. Unless otherwise stated: all reactions, such as handling and storage of products, were carried out under a nitrogen atmosphere; all reactions were carried out at ambient temperature, typically in the range between 18-25° C. with solvents having a purity of at least 98% under anhydrous conditions; yields are given for illustration only and are not necessarily the maximum attainable.

Example 1

Preparation of (5Z,8Z,11Z,14Z,17Z)-icosa-5,8,11,14,17-pentaen-1-ol (2)

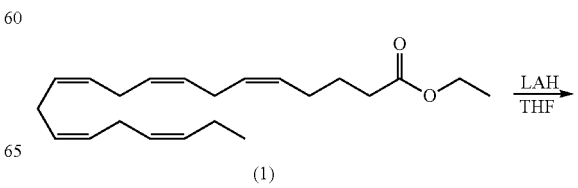

(1)

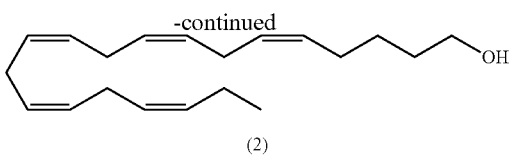

(2)

THF (380 kg) was charged into a reactor and cooled to 10-15° C. An amount of 36.7 kg of a 15% solution of LAH (5.5 kg active content) in a THF-toluene mixture (2.4:1) was added. EPA ethyl ester (1) (80 kg, ≥97% purity) was slowly added, maintaining the temperature at 0-15° C. The reaction mixture was stirred at 0-15° C. until completed.

Ethyl acetate (6.4 kg) was added over a time period of 30-45 minutes at 5-15° C. and the reaction mixture was stirred at 0-15° C. for about 30-40 minutes. An amount of 108 kg of a saturated aq. solution of ammonium chloride and then water (160 kg) were added and the pH was adjusted to about 2 with an aq. 6M HCl solution. The phases were separated and the organic phase was washed with brine (190 kg). The organic phase was evaporated and the toluene content was adjusted to about 22 w/w %. The purity of the title compound (2) was determined to be at least 95% (HPLC).

Example 2

Preparation of 2-((5Z,8Z,11Z,14Z,17Z)-Icosa-5,8,11,14,17-pentaenyloxy)butanoic acid (3)

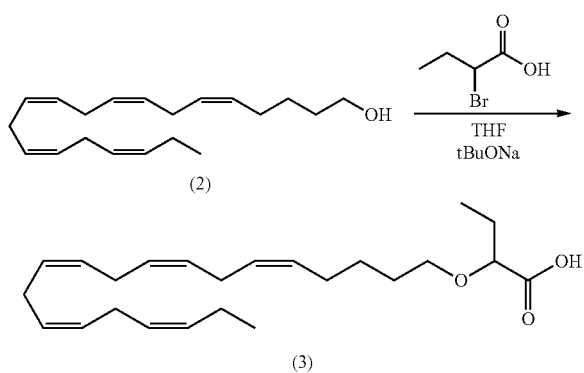

(5Z,8Z,11Z14Z,17Z)-Icosa-5,8,11,14,17-pentaen-1-ol (2) (10 kg, 1.0 eq.), THF (94 kg), and 2-bromobutyric acid (8.6 kg, 1.5 eq.) were charged into a reactor at ambient temperature. The reaction mixture was cooled to 5-10° C. Over a period of 30-60 minutes, 47 kg of a 17% solution of NaOtBu (8 kg active content, 2.4 eq.) in MTBE was added. After the addition was complete, the reaction was stirred for 30 minutes at 5-10. Over a period of 30 minutes, 7.6 kg of a 17% solution of NaOtBu (0.4 eq.) in MTBE was added. After the addition was complete, the reaction was stirred for 60 minutes at 5-10° C. Over a period of 30 minutes, 2-bromobutyric acid (5.8 kg, 1.0 eq.) was added. After the addition was complete, the reaction was stirred for 60 minutes at 5-10° C. Over a period of 30 minutes, 15.9 kg of a 17% solution of NaOtBu (0.8 eq.) in MTBE was added. After the addition was complete, the reaction was stirred for 60 minutes at 5-10° C. Over a period of 30 minutes, 7.7 kg of a 17% solution of NaOtBu (0.4 eq.) in MTBE was added. After the addition was complete, the reaction was stirred for 60 minutes at 5-10° C. The reaction temperature was maintained between 5-10° C., and formic acid (0.8 kg, 0.5 eq.) and water (26.5 kg) were added. The reaction was stirred at 15-25° C., and the pH was adjusted to 2-2.5 using 1:1 concentrated HCl and DI water. The organic and aqueous phases were separated, and the aqueous phase was extracted with MTBE (2×17.6 kg). The combined organic phases were washed three times with DI water (26.6 kg). If necessary the organic phase can be washed a fourth time with DI water. The organic phase was clarified with Celite (2.0 kg) and $Na_2SO_4$ (8.0 kg), and the solids were filtered and washed with MTBE (15 kg). The organic phase was evaporated using a thin film evaporator. The crude product mixture was dissolved in 2-methyltetrahydrofuran (2-MeTHF) (48 kg), and washed three times with a saturated aqueous $NaHCO_3$ solution (28 kg) and then with a saturated aq. NaCl solution (27.5 kg). Optionally, the washing procedure is repeated to remove remaining 2-bromobutyric acid and/or crotonic acid. 2-MeTHF (282 kg) and DI water (285 kg) were added to the crude product, and the pH was adjusted to 12-13 with a 50% aq. NaOH solution to transfer the product to the aqueous phase. The mixture was stirred for 30 minutes, and then the phases were allowed to separate for at least 30 minutes. The phases were separated and 2-MeTHF (280 kg) was added to the aqueous phase and the mixture was stirred for 30 minutes. The phases were again allowed to separate for at least 30 minutes and the phases were separated. The aqueous phase was clarified with Celite (2.2 kg) and charcoal (1 kg), and the solids were filtered and washed with 12 kg of 20% aqueous NaOH. The pH was adjusted to 2-2.5 with conc. HCl(aq.), and the resulting mixture was extracted with MTBE (3×22 kg). The combined organic phases were washed with DI water (30 kg), and the organic phase was clarified with silica (9.4 kg), and the solids were filtered and washed with MTBE (20 kg). The organic phase was concentrated by passing through a thin film evaporator twice. The residue was dissolved in pentane (54 kg), and clarified using silica (0.8 kg) twice, filtering each time and washing with pentane (7 kg). BHA stabilizer (0.03%) was added. The mixture was filtered on 0.5 □m filter, and the solvent was evaporated in vacuo to obtain 2-((5Z,8Z,11Z,14Z,17Z)-icosa-5,8,11,14,17-pentaenyloxy)butanoic acid (3). The total yield starting from EPA ethyl ester (1) was about 53%. The purity was determined to be 96.9% by HPLC.

Example 3

Preparation of 2-((5Z,8Z,11Z,14Z,17Z)-icosa-5,8,11,14,17-pentaenyloxy)butanoic acid (3)

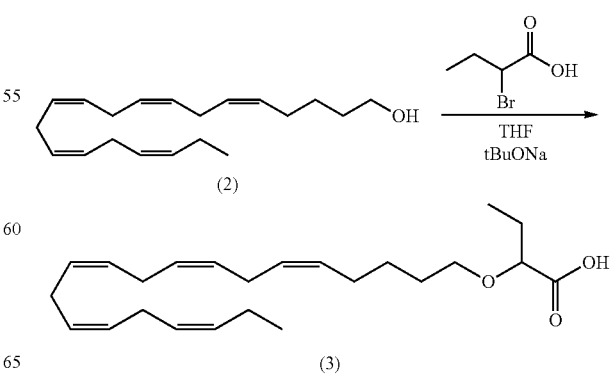

(5Z,8Z,11Z,14Z,17Z)-Icosa-5,8,11,14,17-pentaen-1-ol (2) (25 kg, 1.0 eq.), THF (235 kg), toluene (7 kg) and 2-bromobutyric acid (21.5 kg. 1.5 eq.) were charged into a reactor at ambient temperature. The BHT level was adjusted to 3000 ppm. The reaction mixture was cooled to 5-10° C. Over a period of 30-60 minutes, 117.6 kg of a 17% solution of NaOtBu (20 kg active content, 2.4 eq.) in MTBE was added. After the addition was complete, the reaction was stirred for 30 minutes at 5-10° C. Over a period of 30 minutes, 19.4 kg of a 17% solution of NaOtBu (0.4 eq.) in MTBE was added. After the addition was complete, the reaction was stirred for 60 minutes at 5-10° C. Over a period of 30 minutes, 2-bromobutyric acid (14.5 kg, 1.0 eq.) was added. After the addition was complete, the reaction was stirred for 60 minutes at 5-10° C. Over a period of 30 minutes, 40 kg of a 17% solution of NaOtBu (0.8 eq.) in MTBE was added. After the addition was complete, the reaction was stirred for 60 minutes at 5-10° C. Over a period of 30 minutes, 19.4 kg of a 17% solution of NaOtBu (0.4 eq.) in MTBE was added. After the addition was complete, the reaction was stirred for 60 minutes at 5-10° C. The reaction temperature was maintained between 5-10° C., and formic acid (2 kg, 0.5 eq.) and water (66 kg) were added. The reaction was stirred at 15-25° C., and the pH was adjusted to 2-2.5 using 1:1 concentrated HCl and DI water. The organic and aqueous phases were separated, and the aqueous phase was extracted with MTBE (2×44 kg). The combined organic phases were washed three times with DI water (66 kg). If necessary the organic phase can be washed a fourth time with DI water. The organic phase was dried over $Na_2SO_4$ (20.0 kg) and Celite (5.0 kg) and the solids were filtered and washed with MTBE (15 kg). The organic phase was evaporated using a thin film evaporator. The crude product mixture (Crude A) was dissolved in 2-methyltetrahydrofuran (2-MeTHF) (140 kg), and washed three times with a saturated aqueous $NaHCO_3$ solution (70 kg) and then with a saturated aq. NaCl solution (70 kg). Optionally, the washing procedure is repeated to remove remaining 2-bromobutyric acid and/or crotonic acid. 2-MeTHF (710 kg) and DI water (710 kg) were added to the crude product (Crude B), and the pH was adjusted to 12-13 with a 50% aq. NaOH solution to transfer the product to the aqueous phase. The mixture was stirred for 30 minutes, and then the phases were allowed to separate. The phases were separated and 2-MeTHF (700 kg) was added to the aqueous phase and the mixture was stirred for 30 minutes. The phases were again allowed to separate and the phases were separated. The aqueous phase was clarified with charcoal (2.5 kg) and Celite (5.5 kg), and the solids were filtered and washed with 30 kg of 20% aqueous NaOH. The combined aqueous phase was clarified with Celite (5.5 kg), and the solids were filtered and washed with 30 kg of 20% aqueous NaOH. The pH was adjusted to 2-2.5 with conc. HCl(aq.), and the resulting mixture was extracted with MTBE (3×55 kg). The combined organic phases were washed with DI water (74 kg). The organic phase was concentrated by passing through a thin film evaporator twice. The residue was dissolved in pentane (135 kg), and clarified using silica (2 kg) twice, filtering each time and washing with pentane (17.5 kg). BHA stabilizer (0.03%) was added. The mixture was filtered on 0.5 □m filter, and the solvent was evaporated in vacuo to obtain 2-((5Z,8Z,11Z,14Z,17Z)-icosa-5,8,11,14,17-pentaenyloxy) butanoic acid (3). The total yield starting from EPA ethyl ester (1) was about 65%. The purity was determined to be 96% by HPLC.

Example 4

Purification of crude 2-((5Z,8Z,11Z,14Z,17Z)-icosa-5,8,11,14,17-pentaenyloxy)butanoic acid (3) using CCE The purification was conducted using a filled-column-type extractor; inner diameter: 40 mm, length: 520 mm, filling: ⅛" Dixon-rings (stainless steel). A 10 w/w % solution of crude PRB-01022 (equivalent to Crude A in Example 3) in pentane was introduced at the bottom of the extractor with a flow rate of 20 mL/min and a 67% aqueous methanol solution was introduced at the top of the extractor, also with a flow rate of 20 mL/min. Milton-Roy LMI dosing pumps were used to propagate solutions. After the first run, the level of crotonic acid in the pentane solution was <0.0118 w/w % and the level of 2-bromobutyric acid was 0.49 w/w %. The pentane phase was purified further by repeating the procedure described above. After the second run, the level of crotonic acid in the pentane solution was 0.0002 w/w % (2 ppm) and the level of 2-bromobutyric acid was 0.015 w/w % (150 ppm). The procedure can be repeated to further lower the levels of crotonic acid and 2-bromobutyric acid.

Example 5

Alternative Purification of Crude 2-((5Z,8Z,11Z, 14Z,17Z)-Icosa-5,8,11,14,17-Pentaenyloxy)Butanoic Acid (3) Using Batchwise Extraction Crude 2-((5Z,8Z,11Z,14Z,17Z)-icosa-5,8,11,14,17-pentaenyloxy)butanoic acid (3) (50 g, equivalent to concentrated Crude B in Example 3) was dissolved in pentane (240 mL) and then added MTBE (680 ml), MeOH (200 ml) and DI-water (400 ml). The pH was set to 12-13 with 40% NaOH (aq, 18 mL). The mixture was agitated for 30 minutes before the phases were let to settle. The phases were separated and the aqueous phase was washed twice with MTBE (2×820 mL). To the aqueous phase was then added pentane (200 ml) and the resulting mixture was acidified to pH=2 with a 1:1 mixture of concentrated HCl and water (30 ml). The mixture was agitated and then let to settle. The phases were separated and the organic phase was concentrated in vacuo to yield 43 g product (HPLC purity 95.63%).

Example 6

Purification of Crude 2-((5Z,8Z,11Z,14Z,17Z)-Icosa-5,8,11,14,17-Pentaenyloxy)Butanoic Acid (3) Using CCC Crude 2-((5Z,8Z,11Z,14Z,17Z)-icosa-5,8,11,14,17-pentaenyloxy)butanoic acid (3) (300 mg, equivalent to concentrated Crude B in Example 3) (60% pure by HPLC) were prepared starting from 62% pure (GC) EPA ethyl ester. The crude product was purified running isocratic CCC at reverse phase mode (e.i., the aqueous phase is the mobile phase), using hexane:methanol:water (20:17:3) +0.1% acetic acid as the solvent system. The appropriate fractions were pooled to give the product in 96% purity.

What is claimed is:

1. A method for preparing 2-((5Z,8Z,11Z14Z,17Z)-icosa-5,8,11,14,17-pentaenyloxy)butanoic acid (3) from an eicosapentaenoic acid (EPA) derivative of formula (I) comprising the steps of
a) reducing the EPA derivate of formula (I);

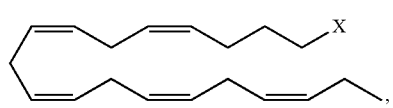 (I)

wherein -X is a carboxylic acid or a carboxylic ester,
to its corresponding alcohol (5Z,8Z,11Z,14Z,17Z)-icosa-5,8,11,14 17-pentaen-1-ol(2) by reduction with a reducing agent

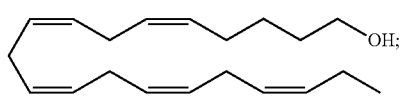 (2)

b) isolating the alcohol (2) from step a);
c) reacting the isolated alcohol (2) from step b) with 2-bromobutyric acid to form 2-((5Z,8Z,11Z,14Z,17Z)-icosa-5,8,11,14,17-pentaenyloxy)butanoic acid (3)

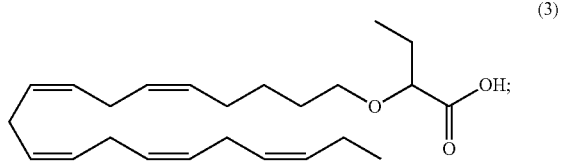 [SMILES: CC/C=C\C/C=C\C/C=C\C/C=C\C/C=C\CCCCOC(CC)C(=O)O] (3)

d) isolating 2-((5Z,8Z,11Z,14Z,17Z)-icosa-5,8,11, 14,17-pentaenyloxy)butanoic acid (3) from step c); and
e) optionally purifying 2-((5Z,8Z,11Z,14Z,17Z)-icosa-5,8,11,14,17-pentaenyloxy)butanoic acid (3).

2. The method of claim 1, wherein -X is a carboxylic acid, and the compound of formula (I) is eicosapentaenoic acid (EPA).

3. The method of claim 2, wherein -X is a carboxylic ester chosen from methyl ester, ethyl ester, and propyl ester.

4. The method of claim 3, wherein the carboxylic ester is ethyl ester and the EPA derivative of formula (I) is EPA ethyl ester (1)

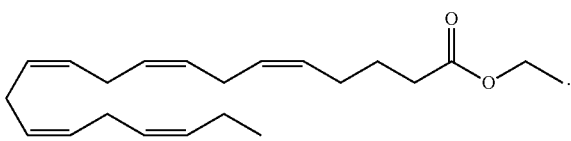 (1)

5. The method of claim 1, wherein the reducing agent is chosen from lithium aluminum hydride (LAH), diisobutylaluminum hydride (DIBAL-H), and diborane ($B_2H_6$).

6. The method of claim 1, wherein the reaction of step a) is carried out in the presence of tetrahydrofuran, diethyl ether, methyl tert-butyl ether, toluene, 1,4-dioxane, 2-methyl tetrahydrofurane, or a mixture thereof.

7. The method of claim 1, wherein the reaction of step a) is carried out at a temperature of about 23 ° C. or below or a temperature ranging from 0 ° C. to 15 ° C.

8. The method of claim 1, wherein isolating (5Z,8Z,11Z,14Z,17Z)-icosa-5,8,11,14,17-pentaen-1-ol (2) in step b) comprises extractive work-up.

9. The method of claim 8, wherein isolating (5Z,8Z,11Z,14Z,17Z)-icosa-5,8,11,14,17-pentaen-1-ol (2) in step b) comprises adding water and adjusting the pH of the aqueous phase to about 2 by addition of an acidic solution.

10. The method of claim 9, wherein isolating (5Z,8Z,11Z,14Z,17Z)-icosa-5,8,11,14,17-pentaen-1-ol (2) in step b) further comprises washing the organic phase with brine, separating the phases, and evaporating the organic solvent.

11. The method of claim 1, wherein the reaction of step c) is carried out in the presence of a base.

12. The method of claim 11, wherein the base is chosen from sodium hydroxide (NaOH), sodium ethoxide (NaOEt), sodium hydride (NaH), and sodium tert-butoxide (NaOtBu).

13. The method of claim 12, wherein the base is NaOtBu.

14. The method of claim 1, wherein the reaction of step c) is carried out in the presence of a solvent chosen from dimethylformamide, tetrahydrofuran, N-methyl-2-pyrrolidone, toluene, xylene, methyl tert-butyl ether, 2-methyltetrahydrofuran, diethyl ether, dimethyl sulfoxide, tert-butanol, and a mixture thereof.

15. The method of claim 1, wherein at least part of the reaction of step c) is carried out at 23° C. or below, at temperature ranging from about 5° C. to 15° C., or at a temperature ranging from about 5° C. to 10° C.

16. The method of claim 1, wherein the step d) comprises aqueous extraction.

17. The method of claim 1, wherein the EPA derivative of formula (I) is derived from a source chosen from vegetable, microbial, animal, and a combination of sources thereof.

18. The method of claim 1, wherein steps a) - e) are conducted to minimize exposure to oxygen.

19. The method of claim 18, wherein steps a) - e) are conducted in an inert atmosphere.

20. The method of claim 1, for preparing 2-((5Z,8Z,11Z,14Z,17Z)-icosa-5,8,11,14,17-pentaenyloxy)butanoic acid (3) from EPA ethyl ester (1) comprising the steps of
a) reducing EPA ethyl ester (1) having a purity of about 97% or about 98%:

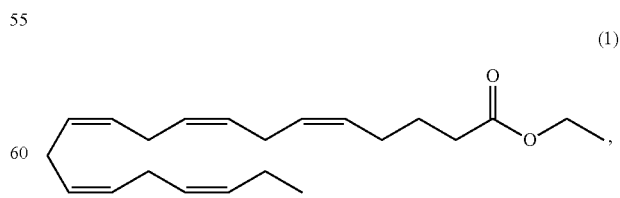 (1)

in the presence of lithium aluminum hydride in tetrahydrofuran at a temperature ranging from 0° C. to 15° C. to its corresponding alcohol (5Z,8Z,11Z,14Z,17Z)-icosa-5,8,11,14,17-pentaen-1-ol (2)

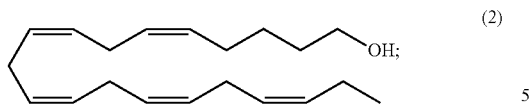
(2)

b) isolating the alcohol (2) from step a) by extractive workup after quenching the reaction by adding ethyl acetate and ammonium chloride;
c) reacting the isolated alcohol (2) from step b) with 2-bromobutyric acid in a mixture of tetrahydrofuran and methyl tert-butyl ether (MTBE) in the presence of sodium tert-butoxide (NaOtBu) at least partly at a temperature of 5° C. to 15° C. to form 2-((5Z,8Z, 11Z, 14Z,17Z)-icosa-5,8,11,14,17-pentaenyloxy)butanoic acid (3)

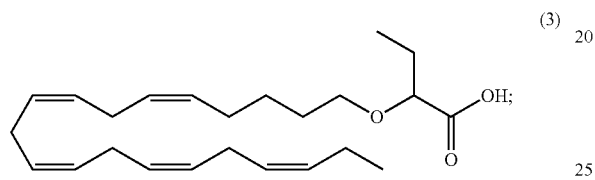
(3)

d) isolating 2((5Z,8Z,11Z,14Z,17Z)-icosa-5,8,11,14,17-pentaenyloxy)butanoic acid (3) from step c) by aqueous extraction; and
e) optionally purifying 2-((5Z,8Z,11Z,14Z,17Z)-icosa-5, 8,1 4,17-pentaenyloxy)butanoic acid (3).

\* \* \* \* \*

UNITED STATES PATENT AND TRADEMARK OFFICE
CERTIFICATE OF CORRECTION

PATENT NO. : 9,365,482 B2
APPLICATION NO. : 14/770870
DATED : June 14, 2016
INVENTOR(S) : Tore Skjæret et al.

It is certified that error appears in the above-identified patent and that said Letters Patent is hereby corrected as shown below:

In the Claims:

In claim 1, column 15, line 2,
"2-((5Z,8Z,11Z14Z,17Z)-icosa-" should read -- 2-((5Z,8Z,11Z,14Z,17Z)-icosa- --.

In claim 20, column 17, line 31,
"icosa-5,8,1 4,17-pentaenyloxy)butanoic acid (3)" should read -- icosa-5,8,11,14,17-pentaenyloxy)butanoic acid (3) --.

Signed and Sealed this
Twenty-third Day of August, 2016

Michelle K. Lee
*Director of the United States Patent and Trademark Office*